(12) United States Patent
Dafni

(10) Patent No.: US 7,390,303 B2
(45) Date of Patent: Jun. 24, 2008

(54) ASSESSMENT OF VASCULAR DILATATION

(76) Inventor: Ehud Dafni, 14 Snapir Street, Caesaria 38900 (IL)

( * ) Notice: Subject to any disclaimer, the term of this patent is extended or adjusted under 35 U.S.C. 154(b) by 614 days.

(21) Appl. No.: 10/676,461

(22) Filed: Sep. 30, 2003

(65) Prior Publication Data

US 2005/0070805 A1    Mar. 31, 2005

(51) Int. Cl.
*A61B 5/00* (2006.01)
*A61B 5/05* (2006.01)
(52) U.S. Cl. .................. 600/500; 600/485; 600/547
(58) Field of Classification Search ............... 600/481, 600/483, 485, 487, 490, 499, 507, 587, 595; 606/201, 202
See application file for complete search history.

(56) References Cited

U.S. PATENT DOCUMENTS

| 4,562,843 | A  | * | 1/1986  | Djordjevich et al. | 600/485 |
| 6,152,881 | A  | * | 11/2000 | Raines et al.      | 600/507 |
| 6,309,359 | B1 | * | 10/2001 | Whitt et al.       | 600/507 |
| 6,554,774 | B1 | * | 4/2003  | Miele              | 600/485 |
| 6,654,628 | B1 | * | 11/2003 | Silber et al.      | 600/410 |
| 7,131,949 | B2 | * | 11/2006 | Hayano et al.      | 600/500 |
| 7,291,112 | B2 | * | 11/2007 | Martin et al.      | 600/485 |
| 2003/0040675 | A1 | * | 2/2003 | Sharrock           | 600/490 |

OTHER PUBLICATIONS

Schachinger, V. et al.; "Prognostic Impact of Coronary Vasolidator Dysfunction on Adverse Long-Term Outcome of Coronary Heart Disease"; Circulation, available on <http://www.circulationaha.org>; Apr. 25, 2000; pp. 1899-1906.

Kadirvelu, A. et al.; "Endothelial Dysfunction in Cardiovascular Diseases"; Medical Progress, May 2002; pp. 4-12.

Sondergaard, E. et al.; "Relationship Between Vascular Dysfunction in Peripheral Arteries and Ischemic Episodes During Daily Life in Patients With Ischemic Heart Disease and Hypercholesterolemia"; Am Heart Julius 144(1), Retrieved from the internet on <http://www.medscape.com/viewarticle/439533_print>; 2002; 8 Pages.

Corretti, M. C. et al.; "Guidelines For the Ultrasound Assessment of Endothelial-Dependent Flow-Mediated Vasolidation of the Brachial Artery"; Journal of the American College of Cardiology; vol. 39; No. 2; 2002; pp. 257-265.

Grimnes, S. et al.; "Bioimpedance and Bioelectricity Basics"; Academic Press; pp. 187-193, 271-275, 1981.

* cited by examiner

*Primary Examiner*—Robert L Nasser

(57) ABSTRACT

A method and apparatus of assessment of relative changes in the cross sectional area of a limb artery. The method includes applying to the artery an external pressure, which causes the cross-sectional area of the artery to change between systole and diastole much more than if the pressure is not applied, determining, over one or more cardiac cycles, a baseline value for a parameter related to the cross-sectional area of the artery, while the pressure is applied, applying a stimulus to the artery, determining, over one or more cardiac cycles, a stimulus-affected value for the parameter related to the cross-sectional area of the artery, while the pressure is applied and while the artery is in a dilated state affected by the stimulus and evaluating the artery based on a comparison of the determined stimulus-affected and baseline values, the baseline value is determined while the artery is substantially not affected by the stimulus.

52 Claims, 10 Drawing Sheets

ASSESSMENT OF VASCULAR DILATATION

FIELD OF THE INVENTION

The present invention relates generally to non-invasive assessment of arterial dilatation.

BACKGROUND OF THE INVENTION

The vascular endothelium is the innermost layer of cells in the blood vessels, located at the interface between the blood and the vessel wall. The cells form a slick layer that prevents blood cell interaction with the vessel wall as blood moves through the vessel lumen. The endothelium plays a critical role in the mechanics of blood flow, the regulation of coagulation, leukocyte adhesion, and vascular smooth muscle cell growth, and also serves as a barrier to the trans-vascular diffusion of liquids and solutes. The endothelium performs many active functions, such as the secretion and modification of vasoactive substances and the contraction and relaxation of vascular smooth muscles.

Endothelial dysfunction is believed to be an important factor in the development of atherosclerosis, hypertension and heart failure. Furthermore, endothelial dysfunction is believed to be an effective predictor of cardiovascular diseases before the disease becomes symptomatic. Hence, there is a high interest in the assessment of the endothelial function in subjects under risk of potential cardiovascular diseases. Publications from recent years show that the endothelial function (or rather, lack thereof) of peripheral arteries is a good predictor for the coronary arterial system.

Some of the publications on the subject are: Volker Schächinger et. al, *Circulation.* 2000;101:1899-1906; Amudha Kadirvelu, et. al, *Medical Progress* May 2002; 4-12.; Eva Sondergaard et. al, *Am Heart J* 144(1): 2002,108-114, the disclosures of which are incorporated herein by reference.

A known method for assessing the endothelial dysfunction of peripheral arteries is described, for example, in Mary C. Corretti et. al. *J Am Coll Cardiol* 2002; 39:257-265, the disclosure of which is incorporated herein by reference. The method includes measurement of a baseline brachial artery diameter using an imaging apparatus (e.g., ultrasound), stimulation of the endothelium to release the vasorelaxing factor nitric oxide (NO), re-measurement of the artery diameter after the stimulation and computation of the change in the arterial diameter. The release of NO results in relaxation of the smooth muscles cells and increases the radius of the blood vessels.

The endothelial function (or dysfunction) is assessed from the relative increase (in %) of the brachial artery diameter relative to baseline due to the stimulation. A typical diameter change for healthy subjects with proper endothelial function is of the order of 7% whereas for subjects with endothelial dysfunction, the diameter change is substantially lower. Other diagnostic indices used relate to the timing of the peak change, rate of return to baseline and area under the relative change.

This test method is hard to implement, due to the difficulty to accurately measure the diameter of the artery using imaging methods and a high skill required from an operator carrying out the method in positioning the apparatus used for the imaging. In practice, although the test is widely recognized as important, it is not widely used.

U.S. Pat. No. 6,152,881 to Rains et. al., the disclosure of which is incorporated herein by reference, describes a method of assessment of endothelial dysfunction, in which the changes in artery volume are determined from changes in the internal artery pressure, as measured by a pressure measurement cuff. The pressure measurement cuff is used to sense the internal artery pressure. The cuff is suggested to be held during the measurement at diastole or near diastole pressure, so that the pressure changes in the cuff reflect the changes in the artery, due to the cardiac cycle. According to the suggested method, NO release is induced by occlusion of the artery for a few minutes and then the pressure in the cuff is monitored for about ten minutes until the artery returns to its normal state. The resultant pressure graph is analyzed to determine the endothelial functioning of the patient. The method of U.S. Pat. No. 6,152,881 requires that the patient remain relatively still for a long period (i.e., about ten minutes).

The method of the U.S. Pat. No. 6,152,881 patent applies pressure to the patient continuously for a relatively long time period, in which return blood flow through the veins is hampered, possibly affecting the measurement results. In addition, if the blood pressure of the patient changes during the measurement, wrong results may be received. In addition, the accuracy of the method is relatively low because it monitors relatively small modulation in the artery diameter.

SUMMARY OF THE INVENTION

An aspect of some embodiments of the invention relates to determining a value of a parameter related to the difference in the cross sectional area of an artery between diastole and systole. The parameter is determined while applying to the artery an external pressure which causes the cross-sectional area of the artery to change between systole and diastole to a much greater extent relative to when the pressure is not applied.

In some embodiments of the invention, the parameter determination is used to compare the cross-sectional area between when a stimulus inducing NO release affects the artery and when the stimulus does not affect the artery. The determination of the parameter for the unaffected artery may be performed before applying the stimulus or after the stimulus effects wear off. Generally, determining the parameter before applying the stimulus allows for a faster measurement procedure, while determining the parameter after the stimulus affects wear off allow for closer conditions and the determinations of the parameter.

Optionally, the parameter is based on an impedance of the body portion including the artery, for example, the parameter may be the modulation amplitude of the impedance. Alternatively, the parameter is based on changes in the pressure and/or the volume of a cuff surrounding a limb including the artery.

In some embodiments of the invention, the applied pressure is between the pressure in the artery at systole and at diastole. Optionally, the applied external pressure is near (e.g., ±10 mmHg) the mean artery pressure (MAP) of the artery. In some embodiments of the invention, the parameter value is determined for a plurality of different applied pressures and according to the resultant parameter values it is determined which of the values (received for which applied pressure) is to be used. In some embodiments of the invention, when parameter values are compared for different stimulus affects, the pressure to be used in each determination of the parameter, is determined separately. Alternatively, the pressure selected for use in a first determination is used also in further determinations.

There is therefore provided in accordance with an exemplary embodiment of the invention, a method of assessment of relative changes in the cross sectional area of a limb artery, comprising applying to the artery an external pressure, which causes the cross-sectional area of the artery to change between systole and diastole much more than if the pressure is not applied, determining, over one or more cardiac cycles, a baseline value for a parameter related to the cross-sectional area of the artery, while the pressure is applied, applying a stimulus to the artery, determining, over one or more cardiac cycles, a stimulus-affected value for the parameter related to the cross-sectional area of the artery, while the pressure is applied and while the artery is in a dilated state affected by the stimulus and evaluating the artery based on a comparison of the determined stimulus-affected and baseline values, the baseline value is determined while the artery is substantially not affected by the stimulus.

Optionally, applying the stimulus comprises restricting flow of blood through the artery. Optionally, restricting flow of blood through the artery comprises occluding the artery. Optionally, a same cuff is used to occlude the artery and to apply the pressure on the artery. Optionally, restricting flow of blood through the artery comprises occluding one or more blood vessels connected to the artery. Optionally, restricting flow of blood through the artery comprises restricting for at least 3 minutes. Optionally, restricting the flow of blood and applying the pressure on the artery are performed using separate cuffs. Alternatively or additionally, applying the stimulus comprises administering a drug to the patient.

Optionally, the baseline value is determined before applying the stimulus. Alternatively, the baseline value is determined after applying the stimulus. Optionally, applying the external pressure comprises applying continuously over at least five cardiac cycles of the patient. Optionally, applying the pressure to the artery comprises applying a local pressure which does not substantially affect other blood vessels in a same limb as the artery.

Optionally, applying the external pressure to the artery comprises applying a pressure which affects an entire cross-section of a limb including the artery. Optionally, applying the external pressure to the artery comprises applying a pressure between the diastole and systole pressure levels of the patient. Optionally, applying the pressure to the artery comprises applying an operating pressure chosen such that the artery collapses in diastole and recuperates in systole. Optionally, applying the pressure to the artery comprises applying a pressure substantially equal to the mean artery pressure of the artery. Optionally, applying the pressure to the artery comprises applying a plurality of different pressure levels and wherein determining the parameter value comprises determining the parameter value for a plurality of different pressure levels. Optionally, applying the plurality of different pressure levels comprises applying a continuously changing pressure.

Optionally, applying a continuously changing pressure comprises estimating a mean artery pressure MAP level, applying a pressure near the estimated MAP level and allowing the pressure to change continuously in a direction leading to the estimated MAP level. Optionally, applying the pressure near the estimated MAP level comprises applying a pressure above or below the mean artery pressure by a predetermined amount. Optionally, allowing the pressure to change comprises allowing the pressure to change until a pressure level distanced from the estimated MAP by a predetermined amount, is reached. Optionally, allowing the pressure to change comprises allowing the pressure to change until the measurements of the parameter fulfill a desired condition and/or until the measurements of the parameter pass their maximum.

Optionally, applying the plurality of different pressure level comprises applying a plurality of discrete pressure levels. Optionally, determining the parameter value comprises determining a bio-impedance and/or a pressure change. Optionally, determining the pressure change comprises measuring the pressure in a cuff used to apply the pressure to the artery and reducing the applied pressure level from the measured pressure. Optionally, the pressure is applied consecutively for at most 20 seconds before release of the pressure.

Optionally, evaluating the artery comprises providing a score indicative of the endothelial function of the artery. Optionally, the score is additionally a function of at least one patient attribute. Optionally, evaluating the artery comprises calculating a change in the cross-sectional area of the artery over a single stimulus-affected cardiac cycle and a single baseline cardiac cycle, responsive to the determination of the stimulus-affected and baseline values, and comparing the calculated changes of the stimulus affected cardiac cycle and of the baseline cycle. Optionally, calculating the change in the cross-sectional area of the artery comprises selecting a single cardiac cycle from the one or more cardiac cycles for which the parameter value was determined and calculating the change for the selected cardiac cycle.

Optionally, selecting the single cardiac cycle comprises selecting a cycle having a maximal change in the parameter value. Optionally, the selecting of the single cardiac cycle is not limited in the beginning point of the cardiac cycle. Optionally, calculating the change in the cross-sectional area of the artery comprises reconstructing an envelope of the maximal and minimal cross-sectional areas of the artery and finding a maximum from the envelope.

Optionally, determining the stimulus affected value for the parameter in the dilated state comprises determining a plurality of values in a plurality of rounds. Optionally, determining the stimulus affected value for the parameter in the dilated state comprises determining a maximum for the plurality of values determined in the plurality of rounds. Optionally, determining the plurality of values in the plurality of rounds comprises determining in rounds separated by rest intervals in which substantial pressure is not applied to the artery. Optionally, determining the plurality of values in the plurality of rounds comprises determining in rounds at predetermined times after the applying of the stimulus.

There is further provided in accordance with an exemplary embodiment of the invention, apparatus for assessment of relative changes in the cross sectional area of a limb artery, comprising a measurement cuff adapted to apply a pressure to an artery, a measurement unit adapted to determine, over one or more cardiac cycles, a value for a parameter related to the cross-sectional area of the artery, while the pressure is applied, a controller adapted to apply to the cuff a pressure that causes the cross-sectional area of the artery to change between systole and diastole much more than if the pressure is not applied, to induce at least two measurement rounds of the parameter by the measurement unit while the pressure is applied; and a processor adapted to compare the values determined by the measurement unit in the at least two measurement rounds.

Optionally, the measurement cuff includes a hydraulic pump adapted to apply the pressure. Optionally, the measurement cuff includes a motor adapted to pull a strap that applies the pressure. Optionally, the processor is further adapted to determine a blood pressure, responsive to parameter values determined by the measurement unit.

Optionally, the controller is adapted to apply an occlusion pressure to the measurement cuff before at least one of the measurement rounds. Optionally, the apparatus includes an occlusion cuff adapted to apply an occlusion pressure to the artery under instructions of the controller. Optionally, the controller is adapted to apply the pressure continuously for a duration of at most 20 seconds. Optionally, the cuff is adapted to apply the pressure substantially around an entire circumference of a limb including the artery. Optionally, the measurement cuff is adapted to apply a local pressure which does not substantially affect other blood vessels in a same limb as the artery.

Optionally, the measurement unit is adapted to measure a bio-impedance. Optionally, the measurement unit includes disposable electrodes. Optionally, the controller is adapted to induce at least one of the measurement rounds responsive to an indication that a stimulus was administered to the artery. Optionally, the controller is adapted to induce at least one of the measurement rounds before the indication that the stimulus was administered to the artery is received. Optionally, the controller is adapted to apply the pressure continuously over at least five cardiac cycles of the patient. Optionally, the controller is adapted to apply a pressure between the diastole and systole pressure levels of the artery.

Optionally, the controller is adapted to apply an operating pressure chosen such that the artery collapses in diastole and recuperates in systole. Optionally, the controller is adapted to apply a pressure substantially equal to the mean artery pressure of the artery. Optionally, the controller is adapted to apply a plurality of different pressure levels during a single measurement round. Optionally, the controller is adapted to apply a continuously changing pressure. Optionally, the controller is adapted to estimate a mean artery pressure level, to apply a pressure above the mean artery pressure by a predetermined amount and to allow the pressure to decrease continuously. Optionally, the controller is adapted to apply a plurality of discrete pressure levels. Optionally, the measurement unit is adapted to determine pressure changes.

Optionally, the apparatus includes an output unit adapted to provide a score indicative of the endothelial function of the artery, responsive to the comparison performed by the processor. Optionally, the score is additionally a function of at least one patient attribute. Optionally, the processor is adapted to calculate a change in the cross-sectional area of the artery over a single cardiac cycle of each of the measurement rounds and to compare the calculated changes of the measurement rounds. Optionally, the processor is adapted to select, for each measurement round, a single cardiac cycle from the one or more cardiac cycles for which the parameter value was determined and to calculate the change for the selected cardiac cycle. Optionally, the processor is adapted to estimate an envelope of the measured parameter values and find a maximal parameter value difference from the envelope. Optionally, the measurement cuff is disposable. Optionally, the measurement cuff includes a disposable inner lining.

There is further provided in accordance with an exemplary embodiment of the invention, apparatus for assessment of artery operation, comprising a first cuff for applying pressure to an artery, a second cuff for applying pressure to an artery; and a controller adapted to control the pressure in both the first and second cuffs.

Optionally, the first and second cuffs are adapted for placement on different locations along a limb. Optionally, the first and second cuffs differ in the cross sectional limb areas they can be placed on. Optionally, the first cuff is adapted to apply pressure over substantially the entire circumference of a limb, while the second cuff is adapted to apply pressure to a limited portion of the circumference of the limb.

Optionally, the controller is adapted to apply the pressure to the first and second cuffs such that pressure is not applied to both the cuffs concurrently.

Optionally, the controller is adapted to apply pressure to the second cuff then to the first cuff and then again to the second cuff. Optionally, the controller is adapted to apply different pressure levels to the first and second cuffs. Optionally, the controller is adapted to apply to the first cuff a pressure suitable to occlude the artery. Optionally, the controller is adapted to apply to the second cuff a pressure between the systole and diastole pressures of the artery. Optionally, the apparatus includes a single air pump adapted to apply pressure to both the cuffs. Optionally, the apparatus includes a single hydraulic pump adapted to apply pressure to both the cuffs. Optionally, the second cuff is additionally used for pressure measurements.

There is further provided in accordance with an exemplary embodiment of the invention, apparatus for assessment of artery operation, comprising a cuff for applying pressure to an artery, a bio-impedance sensing unit for determining the impedance of a portion of a limb including the artery and a controller adapted to apply pressure to the cuff and to measure an impedance through the sensing unit, substantially concurrently.

Optionally, the bio-impedance sensing unit comprises four electrodes. Optionally, the bio-impedance sensing unit comprises an alternating current source and a measurement unit for alternating voltage. Optionally, the alternating current source is adapted to generate currents in a frequency between about 30 KHz and 100 KHz. Optionally, the controller is adapted to determine a blood pressure of the patient responsive to the impedance measurements. Optionally, the controller is adapted to calculate an endothelial functioning score, responsive to the impedance measurements.

There is further provided in accordance with an exemplary embodiment of the invention, a method of assessment of blood pressure, comprising placing a bio-impedance probe above an artery of a patient, measuring impedance values through the bio-impedance probe and determining the blood pressure of the patient responsive to the measured impedance values.

Optionally, the method includes applying pressure to the artery while the impedance values are measured. Optionally, the applied pressure changes between a level above systole and a level below diastole.

There is further provided in accordance with an exemplary embodiment of the invention, a method of assessment of relative changes in the cross sectional area of a limb artery of a patient, comprising applying to the artery an external pressure, having a value between systole and diastole of the patient and determining a value for a parameter indicative of the change in the cross-sectional area of the artery between diastole and systole, over one or more cardiac cycles, the parameter value is determined without using measurements from when an external pressure above systole level or below diastole level, was applied.

Optionally, applying the external pressure comprises applying a constant pressure. Optionally, applying the external pressure comprises applying a pressure varying within a range including less than half the range between diastole and systole pressure of the patient.

BRIEF DESCRIPTION OF FIGURES

Particular non-limiting embodiments of the invention will be described with reference to the following description of embodiments in conjunction with the figures. Identical structures, elements or parts which appear in more than one figure are preferably labeled with a same or similar number in all the figures in which they appear, in which.

DETAILED DESCRIPTION OF EMBODIMENTS

Figure 1:
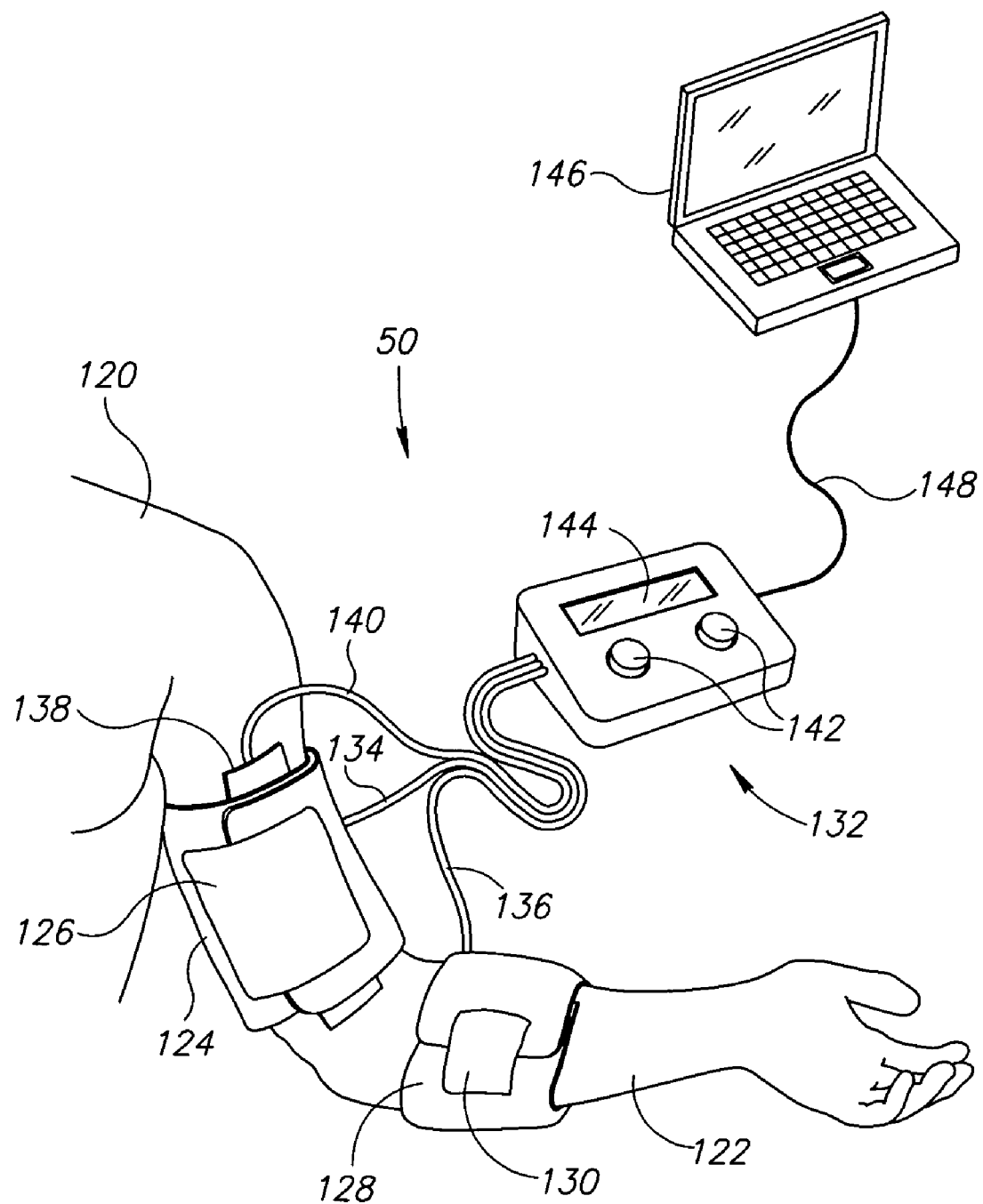
FIG. 1 is a schematic illustration of a system for assessing endothelial function, in accordance with an exemplary embodiment of the invention.

FIG. 1 is a schematic illustration of a system 50 for assessing endothelial dysfunction, in accordance with an exemplary embodiment of the invention. System 50 comprises a measurement cuff 124 which is adapted for mounting on an upper arm of a patient 120. Optionally, measurement cuff 124 is fastened to the upper arm by a strap 126. Alternatively, any other method is used to fasten measurement cuff 124 to the patient's arm. Measurement cuff 124 is used to apply a pressure required for measurement to the arm. In some embodiments of the invention, a bio-electrical sensor unit 138 is mounted on the upper arm within cuff 124, for measuring the cross-sectional area of the artery of the arm. Alternatively, as described below, measurement cuff 124 is used itself for measuring the artery cross-sectional area, as described below.

In some embodiments of the invention, system 50 includes an occlusion cuff 128 for inducing release of the vasorelaxing factor NO. In an exemplary embodiment of the invention, occlusion cuff 128 is adapted for mounting on the forearm 122 of patient 120 and is fastened by a strip 130 to the arm. System 50 further includes a control unit 132. Control unit 132 is optionally connected to sensor unit 138 through a cable 140 and to cuffs 124 and 128 through air tubes 134 and 136, respectively.

Control unit 132 optionally includes a user input interface 142 and a display 144. In some embodiments of the invention, control unit 132 may be connected to a computer 146, via a cable 148, for configuration and/or data download. Computer 146 may be, for example, dedicated for use with system 50, a personal computer in a physician's clinic, part of a hospital network and/or a remote computer connected, for example, through the Internet or an intranet. For example, a computer network connection may be used for receiving patient data and/or providing test results to remote locations. In some embodiments of the invention, computer 146 manages a database of test results classified according to demographic and/or epidemiologic data for the purpose of determining endothelial dysfunction trends and/or for comparing current test results to previously acquired results from same or different patients.

In some embodiments of the invention, measurement cuff 124 and/or occlusion cuff 128 have adjustable sizes, so that they can be used on a plurality of different size patients. Alternatively or additionally, system 50 includes a plurality of different size cuffs, from which cuffs fitting the patient are chosen. In some embodiments of the invention, disposable cuffs are used. Alternatively, cuffs 124 and/or 128 include a replaceable inner lining, which is replaced for each patient. Similarly, sensor unit 138 may be disposable or may allow for mounting of disposable bio-impedance electrodes.

In some embodiments of the invention, cuffs 124 and/or 128 include markings that indicate proper placement and/or orientation of the cuffs. Alternatively or additionally, after placement, the placement of measurement cuff 124 (and/or cuff 128) is marked, such that the cuff may be returned to place if it moves during a test session. The marking may be performed using suitable stickers and/or a pen for marking on skin.

Figure 2:
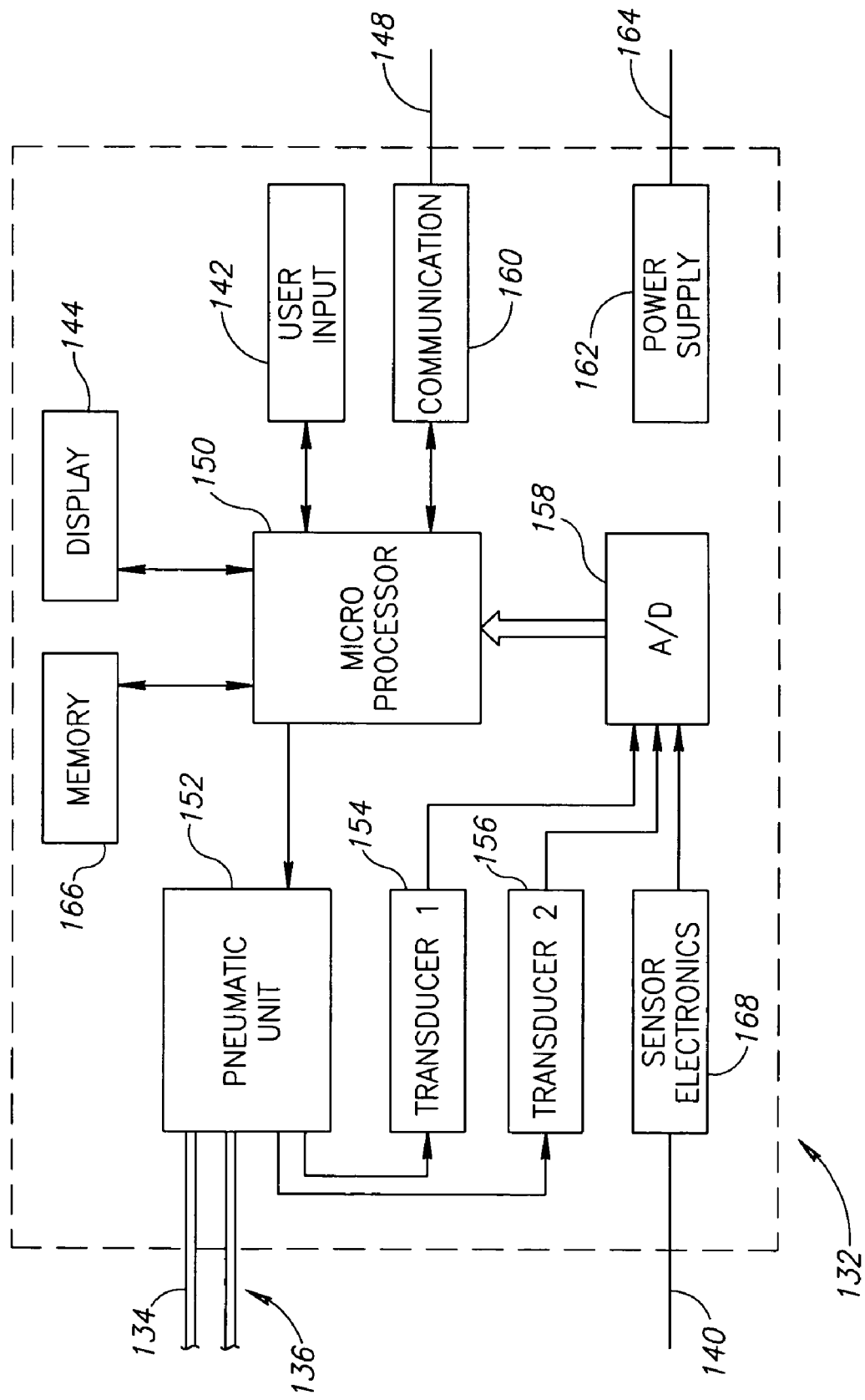
FIG. 2 is a simplified block diagram of a control unit of the system of FIG. 1, in accordance with an exemplary embodiment of the invention.

FIG. 2 is a block diagram of control unit 132, in accordance with an exemplary embodiment of the invention. A microprocessor 150 optionally serves as the heart of control unit 132, controlling all the units of the control unit. Control unit 132 includes a pneumatic unit 152, which operates to inflate or deflate cuffs 124 and 128, and pressure transducers 154 and 156 which measure the pressures in cuffs 124 and 128, respectively. A sensor electronics unit 168 optionally provides commands to sensor unit 138 and receives readings from the sensor unit. An analogue to digital converter (A/D) 158 optionally converts the readings of pressure transducers 154 and 156 and/or sensor electronics unit 168 into digital samples provided to microprocessor 150.

In an exemplary embodiment of the invention, pressure transducers 154 and 156 comprise sensors such as manufactured by Motorola™ and marketed under the brand name of MTX2201, although other transducers of air pressure could also be used.

Microprocessor 150 optionally also communicates with display 144 and user input interface 142. In some embodiments of the invention, a communication block 160 is used to communicate with an external computer 146 or any other external unit. Power is optionally provided to control unit 132 by a power supply 162 which may receive external power through a cable 164 and/or may include batteries. Patient examination results and other data are optionally stored in an internal memory 166.

Figure 3:
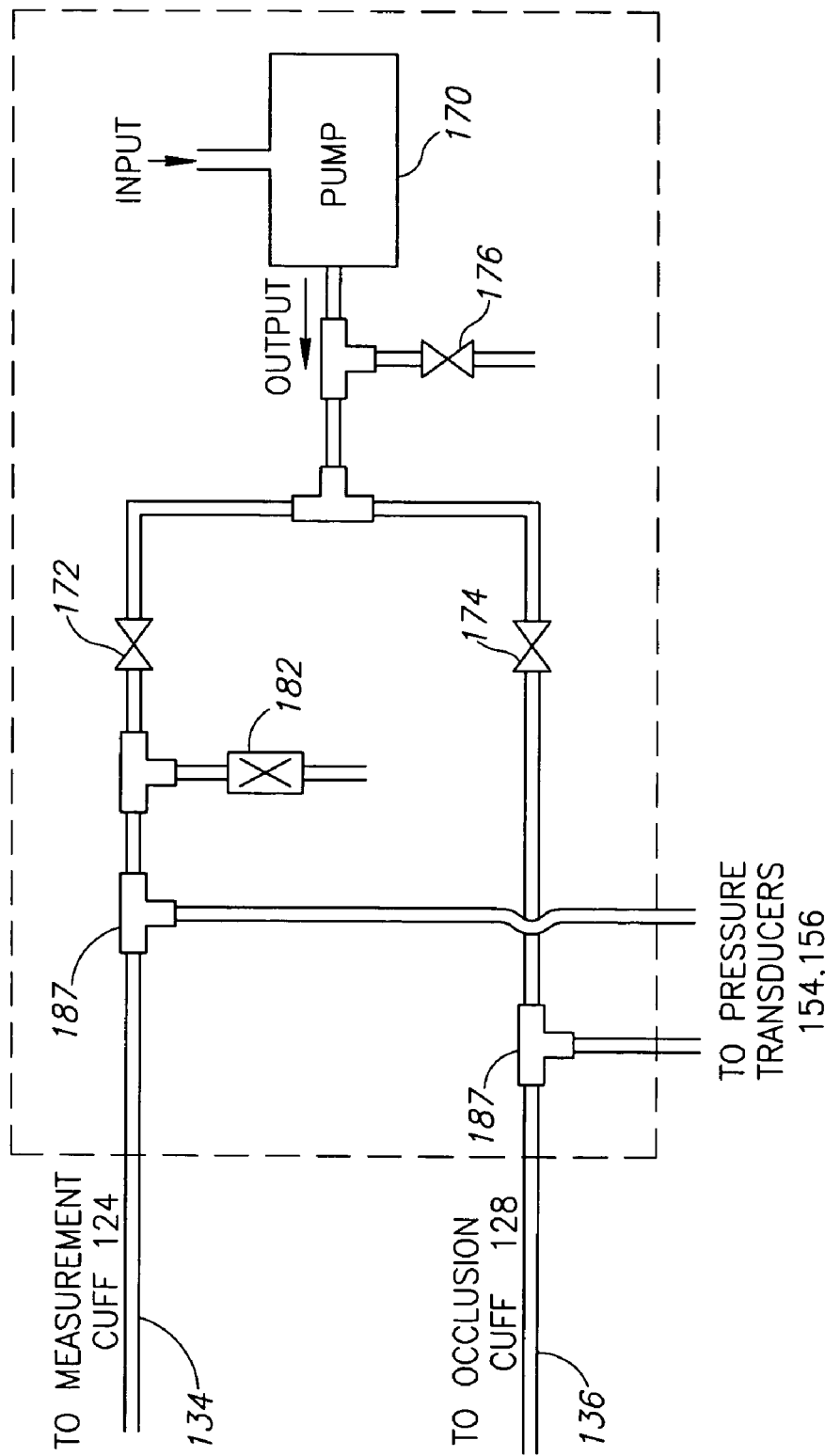
FIG. 3 is a simplified schematic layout of a pneumatic unit, in accordance with an exemplary embodiment of the invention.

FIG. 3 is a schematic layout of pneumatic unit 152 (FIG. 2), in accordance with an exemplary embodiment of the invention. Pneumatic unit 152 includes an air pump 170 optionally adapted to provide output pressure up to a pressure which completely occludes blood flow through the arm (e.g., about 280-320 mmHg above ambient pressure). Valves 172 and 174 optionally control the flow of pressurized air from pump 170 to measurement cuff 124 and occlusion cuff 128, respectively, under instructions from microprocessor 150. A valve 176 is optionally closed when air pressure is provided to either of cuffs 124 or 128 and is opened when air pressure is not to be supplied to either of the cuffs. A flow restrictor 182, such as a section of thin tube or a small aperture, is provided for slow release of pressure from measurement cuff 124. Flow restrictor 182 is optionally always open and is tuned to allow for pressure reduction in measurement cuff 124 at a relatively slow rate, for example between about 3-4 mmHg per second. T-connectors 187 optionally connect cuffs 124 and 128 respectively to pressure transducers 154 and 156, which measure the air pressure within the cuffs.

Figure 4:
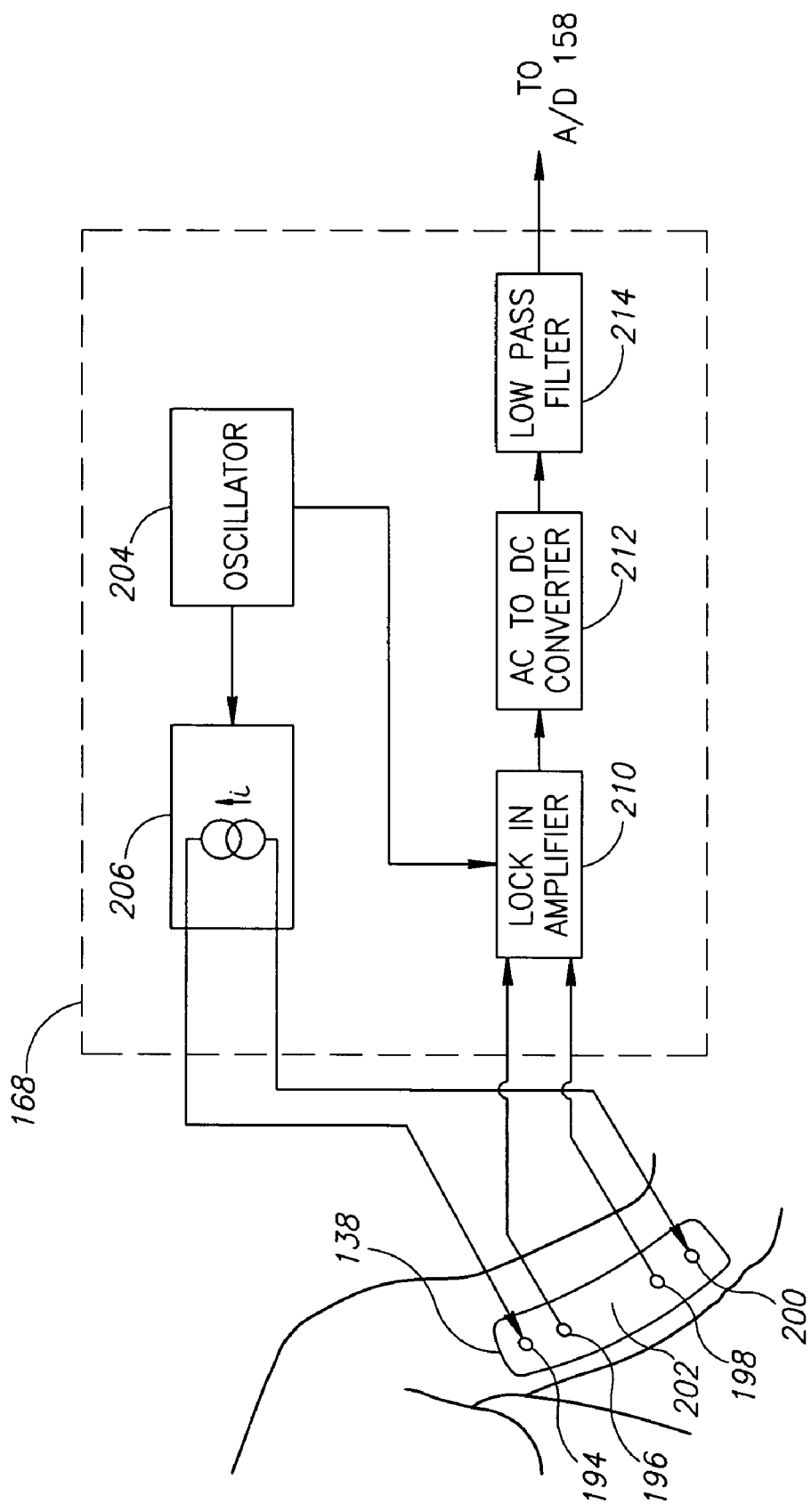
FIG. 4 is a simplified schematic illustration of a sensor unit and a sensor electronics unit, in accordance with an exemplary embodiment of the invention.

FIG. 4 is a schematic illustration of sensor unit 138 and sensor electronics unit 168, in accordance with an exemplary embodiment of the invention. Sensor unit 138 optionally includes four spot bio-electrodes 194, 196, 198 and 200, such as used for ECG, in an arrangement for bio-electrical measurements. The electrodes are optionally mounted on a relatively rigid backplane 202 in a straight line, electrodes 194 and 200 being farthest away from each other. In an exemplary embodiment of the invention, electrodes 194 and 200 are equally distanced from electrodes 196 and 198, respectively. Backplane 202 is optionally sufficiently rigid so that the distances between the electrodes do not change substantially. Alternatively to using backplane 202, the electrodes are placed directly on measurement cuff 124. In an exemplary embodiment of the invention, electrodes 194 and 200 are distanced from each other by about 120 mm and electrodes 196 and 198 are distanced by about 100 mm. Backplane 202 has a size of, for example, 140×30 mm.

Sensor electronics 168 optionally includes an oscillator 204 and a current source 206 delivering alternating current between source electrodes 194 and 200. In an exemplary embodiment of the invention, the provided current is about 1 mA at a frequency between about 30-100 KHz (e.g., about 50 KHz). At these frequencies, the cell membranes have a relatively high frequency, such that the changes in impedance are mainly due to the changes in the blood volume which has a much lower impedance. The source current optionally has a stability of about 1%, as is conventional in bio-impedance measurements. Sensor electronics 168 optionally further includes a lock-in amplifier 210, connected to measurement electrodes 196 and 198. Lock in amplifier optionally also receives a reference signal from oscillator 204. The output signal from lock in amplifier 210 is optionally converted to a DC voltage signal by a converter 212 and is conditioned by a low pass filter 214. Low pass filter 214 optionally removes components at rates substantially above the rate of the cardiac cycle, e.g., above 20 Hz. The output of filter 214 is fed to A/D 158 (FIG. 2).

Alternatively or additionally, sensor electronics 168 may include any other arrangement known in the art for measuring electrical impedance, such as described in "Bioimpedance and Bioelectricity Basics" by Sverre Grimnes and Orjan Grottem Martinsen, Academic Press (2000), pages 187-193 and 270-275, the disclosure of which is incorporated herein by reference.

The specific embodiment of the sensor electronics 168 and sensor unit 138 are described herein only by a way of example. Experts in the field will appreciate that other bio-impedance measurement methods and apparatus may be used, including operating at other frequencies and/or current levels and/or using other electrode arrangements.

Figure 5:
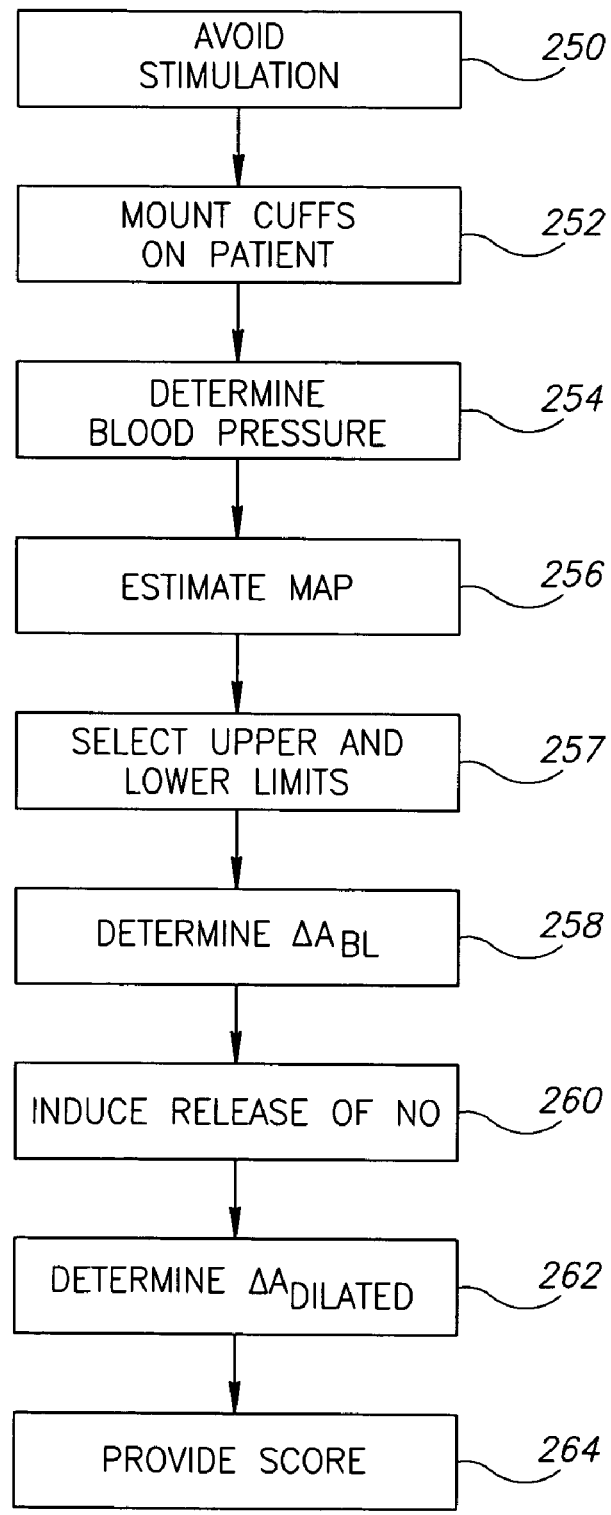
FIG. 5 is a flowchart of acts performed in an endothelial function assessment test, in accordance with an exemplary embodiment of the invention.

FIG. 5 is a flowchart of acts performed in an endothelial dysfunction assessment test session, in accordance with an exemplary embodiment of the invention. Patient 120 optionally avoids (250) stimulations which may interfere with the test, for a predetermined time before the test. For example, the patient may be required to avoid eating, taking medicine, smoking and/or drinking coffee for two hours or more before the test. In addition, the patient optionally lies at rest, in a supine position, for at least 15 minutes before the test, as well as during the test.

An arm 122 on which the test is performed is optionally stretched aside from the body and supported. Measurement cuff 124, including sensor unit 138, is mounted (252) on the upper arm and occlusion cuff 128 is mounted on the forearm of patient 120. Sensor 138 is optionally pressed against the inner side (the side facing the patient's chest) of the upper arm, as close as possible to the artery on the outer surface of the patient's arm. A conductive gel is optionally used to improve the contact of the electrodes of sensor 138 to the skin of the arm.

The blood pressure of the patient is optionally determined (254) using any method known in the art and/or using system 50 as described hereinbelow. The mean artery pressure (MAP) is estimated (256) based on the measured blood pressure of the patient. Alternatively, the mean artery pressure (MAP) is determined directly as the pressure at which the largest change in the artery cross section occurs, as described hereinbelow. Upper and lower limits around the estimated MAP are selected (257), for example forming a range of a predetermined size around the MAP, defining a range of external pressures for which measurements are to be acquired.

A base line difference value representative of the difference in the brachial artery cross sectional area between systole and diastole ($\Delta A_{BL}$) is then determined (258), in a base line phase of the test session. Details of the determination of the brachial artery cross sectional area difference are discussed below with reference to FIG. 7. Thereafter, release of NO is induced (260) using any of the methods known in the art and/or discussed below. A value of the brachial artery cross-sectional area difference ($\Delta A_{dilated}$) is determined again (262) under the dilated conditions, due to the release of NO, in a dilated phase of the test session. The dilated cross-sectional area difference is optionally determined in a manner similar to the determination of the base line difference, for example as described below with reference to FIG. 7. The increase in the brachial artery cross-sectional area difference under the dilated conditions relative to the baseline value is used to provide (264) a score representative of the endothelial dysfunction state of the patient. The score is optionally provided on display 144 and/or is transferred to computer 146.

In some embodiments of the invention, the difference in the brachial artery cross sectional area is based on changes in the measured impedance of the arm. Alternatively, the difference value is based on changes in measurements of the volume of the artery, as reflected by changes in the pressure of measurement cuff 124. Details of these embodiments of the determination of the difference are described herein below. It is noted that, in some embodiments of the invention, the difference in the cross sectional area is provided in arbitrary units, depending on the measurement method used. Arbitrary units may be used, since the cross-sectional difference values are compared to each other and not to predetermined results. It is noted, however, that the results may be converted into area units, for example by calibrating the pressure changes with the artery volume changes, for example as described in the above mentioned U.S. Pat. No. 6,152,881. In an exemplary embodiment of the invention, both bio-impedance measurements and imaging measurements are collected from a plurality of subjects and according to the results, a conversion table is generated. Microprocessor 150 is then calibrated with a conversion table based on the measurement results from the plurality of subjects. The conversion table optionally has different entries for patients of different attributes, such as different gender, age, height and/or weight.

Referring in more detail to estimating (256) the mean artery pressure (MAP), in some embodiments of the invention, the MAP is determined using a blood pressure monitor using methods known in the art. Alternatively, the estimated MAP is calculated from the systolic blood pressure SYS and diastolic blood pressure DIA, for example using the equation:

MAP=(2×DIA+SYS)/3

Referring in more detail to selecting (257) the upper and lower limits, in some embodiments of the invention, the upper and lower limits are set according to a largest expected error in the estimating of the MAP, such that the actual MAP will be in the measurement range. Alternatively or additionally, the upper and lower limits are selected according to an expected drift in the MAP during the measurements (for example, due to changes in the patient's blood pressure), such that the actual MAP will be in the measurement range throughout the measurement period. In some embodiments of the invention, the size of the measurement range is selected such that the measurements may be completed in a reasonable amount of time, which will not burden the patient. The size of the measurement range is optionally selected such that it covers a predetermined number of cardiac cycles, at the rate at which the pressure is changed. In an exemplary embodiment of the invention, the upper and lower limits are set between about 10-20 mmHg above and below the estimated MAP. In some embodiments of the invention, the size of the range is selected according to attributes of the patient. For example, a shorter range may be used for a patient with a high-rate heart cycle.

Referring in more detail to inducing (260) the NO release, in some embodiments of the invention, the NO release is induced by occluding the blood flow through the brachial artery for a period of between about 3-5 minutes. Optionally, the occlusion is affected by applying a pressure of between 250 and 300 mmHg through occlusion cuff 128. In some embodiments of the invention, in applying the occlusion, valves 176 and 172 (FIG. 3) are closed and valve 174 is open. Pump 170 is operated to inflate occlusion cuff 128 to the desired pressure. When the desired pressure is reached, valve 174 is closed, the operation of pump 170 is stopped and valve 176 is opened. At the end of the occlusion period, valve 174 is opened and the air pressure in occlusion cuff 128 is released through valve 176.

Alternatively to occluding the same artery on which the measurements are performed, a different artery connected to the measured artery, is occluded. For example, when the measurements are performed on the brachial artery, the occlusion may be applied to the radial and/or ulnar arteries.

Alternatively to inducing NO release by occlusion, the NO release is induced by administering by arterial infusion of an endothelium stimulating substance (e.g., an NO-agonist), such as acetylcholine, to the artery.

The base line phase optionally includes a plurality of rounds (e.g., 2-3 rounds), in each of which the base line arterial area difference ($\Delta A_{BL}$) is determined. The results of the plurality of measurement rounds are optionally averaged to provide the base line arterial area difference ($\Delta A_{BL}$). The averaging is expected to reduce random noise in the measurements. Alternatively, a single measurement is performed in order to limit the time required for the measurement session.

In some embodiments of the invention, the dilated measurement phase includes a single measurement round in which the dilated cross-sectional arterial area difference ($\Delta A_{dilated}$) is determined (262) a predetermined time after the inducing of NO release, when the effect of NO is expected to be maximal. In an exemplary embodiment of the invention, the measurement round of $\Delta A_{dilated}$ is performed between about 60-90 seconds after the occlusion is released. Alternatively or additionally, a plurality of measurement rounds of $\Delta A_{dilated}$ are performed in the dilated measurement phase, in order to determine the time between applying the stimulus and reaching the peak cross-sectional difference area and/or the time until the artery returns to normal. In an exemplary embodiment of the invention, measurement rounds are performed around 30, 60, 90, 120, 180 and 300 seconds after the release of the occlusion. Optionally, the measurement rounds begin a little before the designated times, such that the MAP pressure is reached 30, 60, 90, 120, 180 and 300 seconds after the occlusion is released, since at these time ranges the effects of the dilation are expected to reach local maximums.

The dilated cross-sectional arterial area difference ($\Delta A_{dilated}$) is optionally determined as an average of the determined values of the repeated rounds. Alternatively, the maximal value, which represents the maximal effect of the NO release, is used.

The repeated measurement rounds of the dilated cross-sectional arterial area difference ($\Delta A_{dilated}$) are optionally performed at times separated from each other sufficiently, so that the blood flow to the arm is not continuously occluded during the dilate measurement phase. In an exemplary embodiment of the invention, beginning of measurement rounds are separated by at least 30 seconds, so that between each round of up to about 20 seconds, there are at least 10 seconds in which the blood flow is not disturbed. This prevents the repeated measurement rounds from inducing hyperemia which would influence the measurements and/or prevents the repeated measurement rounds from causing discomfort to the patient.

Referring in detail to providing (264) a score representative of the endothelial dysfunction, in some embodiments of the invention, the score is based on the ratio of the dilated difference ($\Delta A_{dilated}$) and the baseline difference ($\Delta A_{BL}$). Optionally, the score is given by:

Score=($\Delta A_{dilated}$)/($\Delta A_{BL}$)−1

Typical results for a healthy patient achieve a score of between about 0.05-0.07, while for a patient suffering from endothelial dysfunction a score of about 0.02-0.03 or lower, is expected.

In some embodiments of the invention, the score is compared to a threshold and accordingly a binary diagnosis is provided (e.g., normal, abnormal). In some embodiments of the invention, the threshold depends on one or more attributes of the patient, such as gender, height, weight and/or age. Alternatively or additionally, a multi-level diagnosis is provided, for example giving a value in percentages or other units. The multi-level diagnosis is optionally determined by comparing the score to an array of thresholds.

Alternatively or additionally to providing a score depending on the relative cross-sectional area, the score depends on the time after applying the stimulus at which the cross-sectional area difference is maximal and/or on the time after applying the stimulus at which the artery returns to normal. Further alternatively or additionally, the score depends on the integrated added cross-sectional area of the artery, due to the stimulus. In healthy patients, the integrated area is generally larger than in sick patients.

As mentioned above, during the test session, between the base line phase and the dilated phase, the patient remains at rest, so as to minimize the difference in conditions between the measurements. Alternatively or additionally, the results are corrected for changes in the conditions between the phases.

Figure 6:
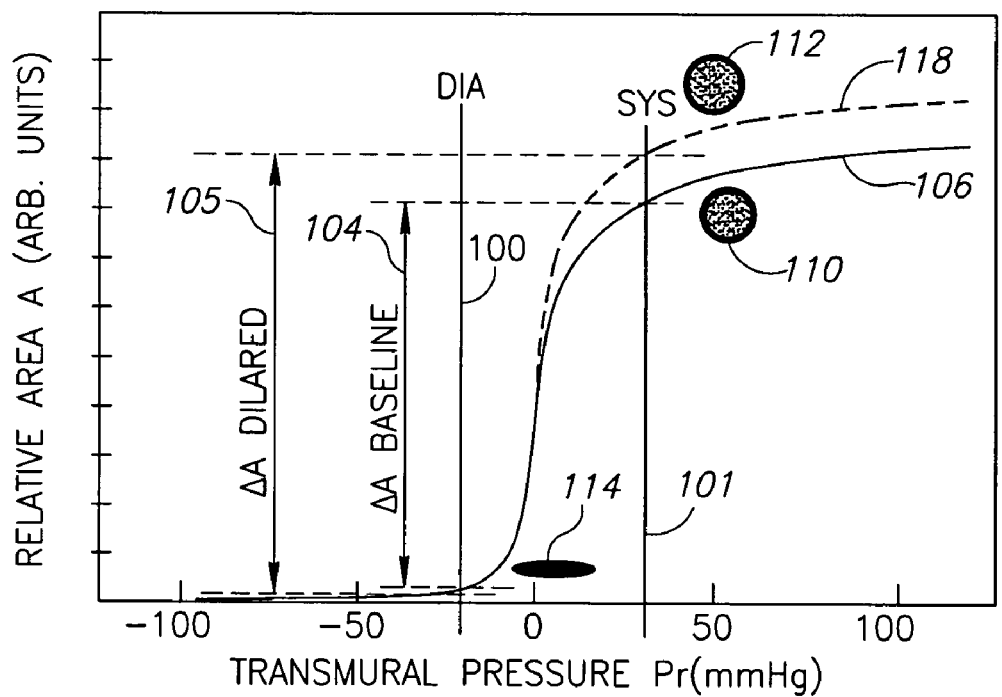
FIG. 6 is a schematic graph of the area (A) of the brachial artery as a function of the transmural pressure affecting the artery, in a dilated artery and a non-dilated (baseline) artery, in accordance with exemplary measurement results.

FIG. 6 is a schematic graph of the area (A) of the brachial artery as a function of the transmural pressure (i.e., the total pressure) affecting the artery, in a dilated artery and a non-dilated (baseline) artery. The transmural pressure is formed from the internal blood pressure which applies a force directed radially out of the artery and the external pressure applied to the artery using measurement cuff 124, which is directed opposite the internal pressure. The transmural pressure, when there is no external pressure applied to the patient's arm, is equal to the internal pressure, which as is known in the art, typically ranges between about 50-160 mmHg, according to the blood pressure of the patient. As can be seen from line 106, which illustrates the area of the artery in a baseline artery, absent an external pressure, the area of the artery changes only slightly over the cardiac cycle.

When the external pressure, however, is close to the mean artery pressure (MAP), the mean transmural pressure is close to zero and the artery cross-sectional area changes drastically during the cardiac cycle. Generally, the artery changes during the cardiac cycle, under such conditions, between a normal state and a substantially collapsed state. The range of the cardiac cycle is indicated schematically by perpendicular lines 100 and 101, for a substantially zero transmural pressure. Line 100 corresponds to the diastole phase, when the MAP is zero, and line 101 corresponds to the systole phase, when the MAP is zero.

Thus, due to the external pressure, the cross-sectional area of the artery changes drastically over the cardiac cycle and it is easier to identify changes in the cross-sectional area of the artery. Generally, the cross sectional area modulation amplitude $\Delta A$ has a maximum value when the mean transmural pressure is approximately zero. For higher or lower mean transmural pressure, the change in artery cross sectional area between the diastolic and systolic phase is generally smaller. Since the blood pressure of the subject may change during the examination of the patient, it is advantageous in each measurement to identify the external pressure at which $\Delta A$ is maximal and perform the measurement at that pressure, so different measurements are performed at the same mean transmural pressure.

The peak cross sectional area in the baseline state, represented by shape 110, is smaller than the peak cross sectional area in the dilated state, represented by shape 112. During the diastolic phase the artery collapses, yielding a close to null cross sectional area in both baseline and dilated states, as shown diagrammatically by shape 114. Furthermore, the cross sectional area in the diastolic phase is presumably smaller in the dilated state than in the baseline state since the relaxed artery makes a stronger collapse but this effect is less significant than the effect in the systolic phase. According to the invention, the ratio between the cross sectional area modulation amplitude at the dilated state ($\Delta A_{dilated}$) 105 and the cross sectional area modulation amplitude at the baseline state ($\Delta A_{BL}$) 104 is a quantitative index of the dilating process.

Figure 7:
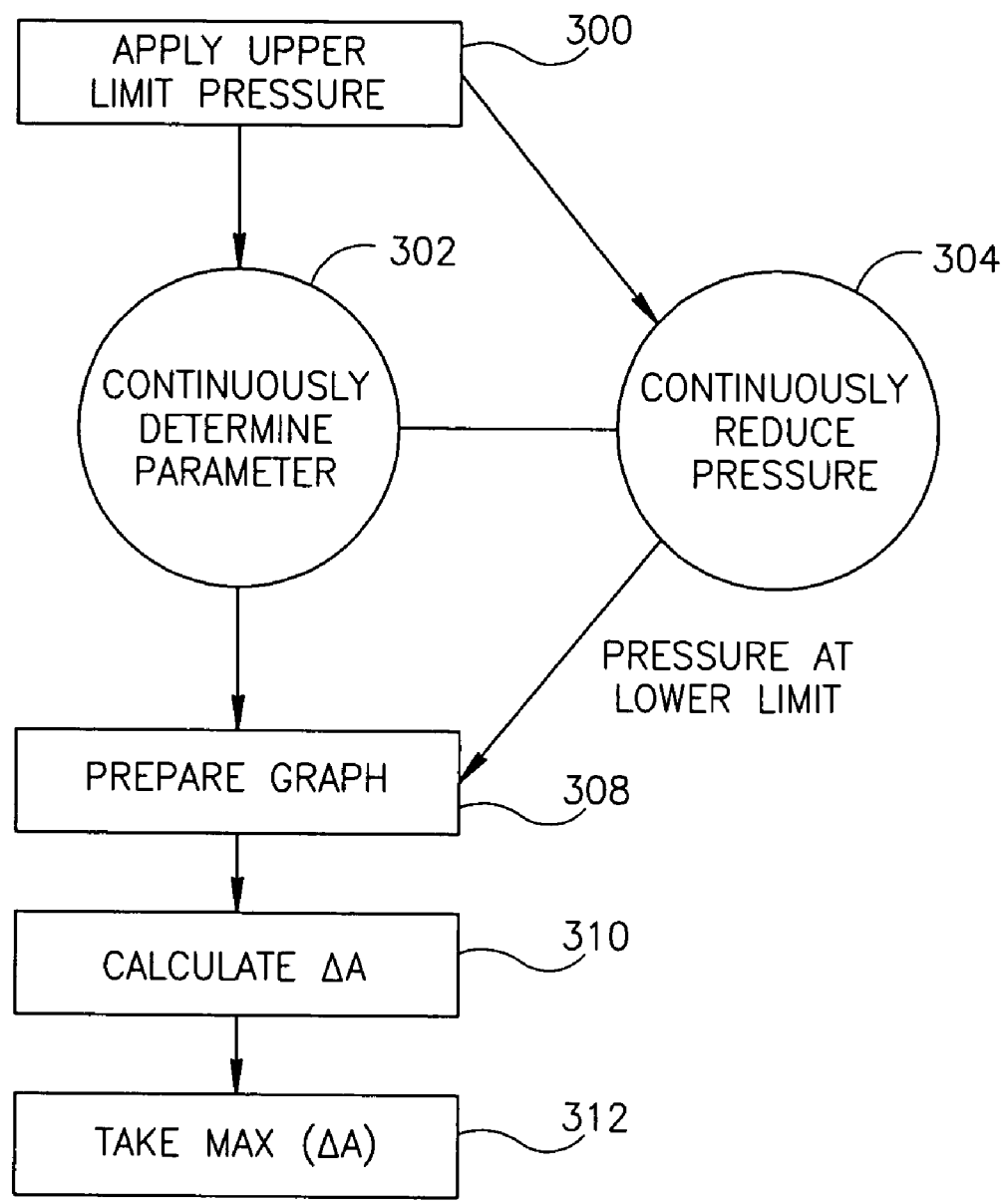
FIG. 7 is a flowchart of acts performed in determining an artery cross-sectional area difference, in accordance with an exemplary embodiment of the invention.

FIG. 7 is a flowchart of acts performed in measurement round of determining the brachial artery cross-sectional area difference, in accordance with an exemplary embodiment of the invention. The method of FIG. 7 is optionally used for rounds of determining the dilated ($\Delta A_{dilated}$) or the baseline ($\Delta A_{BL}$) brachial artery cross-sectional area difference. A pressure at the selected (257, FIG. 5) upper limit of the defined pressure range, is applied (300) to measurement cuff 124. Control unit 132 begins to continuously determine (302) and register a parameter of the cross sectional area of the brachial artery. Due to the pressure release (304) through flow restrictor 182, the pressure in measurement cuff 124 continuously reduces. The determination (302) of the parameter is optionally performed continuously until the pressure in measurement cuff 124 reaches the selected lower limit.

In an exemplary embodiment of the invention, at the time of applying (300) the upper limit pressure, valves 174 and 176 (FIG. 3) are closed and valve 172 is opened. Pump 170 is operated to inflate measurement cuff 124 to the upper limit pressure. When the upper limit pressure is reached, valve 172 is closed, the pump is stopped and valve 176 is opened. The pressure in measurement cuff 124 continuously decreases due to the air release through flow restrictor 182. As long as the cuff pressure does not go beneath the lower limit, pressure data from transducer 154 and/or sensor data from sensor electronics unit 168 are digitized and acquired (302). When the pressure in measurement cuff 124 reaches the lower limit, the data registration is stopped, valve 172 is opened and the pressure of measurement cuff 124 is released through valve 176.

The pressure release through flow restrictor 182 is optionally slow enough and/or the selected upper and lower pressure limits are sufficiently distanced so that the measurements are performed over a plurality of cardiac cycles. In an exemplary embodiment of the invention, the pressure release rate is between about 3-4 mmHg/sec, and the measurements are performed over between about 6-8 cardiac cycles and/or over between about 7-10 seconds. In another exemplary embodiment of the invention, the parameter is determined (302) over between about 10-20 cardiac cycles and/or over about 10-15 seconds. Optionally, pump 70 has an output flow rate sufficient for achieving a pressure of about 180 mmHg in measurement cuff 124, within about 5 seconds of pumping or less. Thus, the entire measurement procedure of FIG. 7, including inducing the pressure in measurement cuff 124, requires up to about 20 seconds.

After the lower limit pressure is reached, a graph of the parameter of the cross sectional area of the artery, as a function of time and/or pressure, is prepared (308) based on the registered cross sectional measurements. The largest difference in the cross-sectional area ($\Delta A$) of the artery, during a single cardiac cycle, is optionally calculated (310, 312) from the determined graph over the plurality of cardiac cycles. Using the maximum value provides a higher value which allows easier measurement and a better contrast. Additionally, using the maximum value, provides an anchor point at which the baseline measurements and the dilatation measurements are comparable.

In some embodiments of the invention, the difference in the cross sectional area ($\Delta A$) is calculated (310) by determining an envelope of the measurements and finding a maximum difference of the cross-sectional area in the envelope. The calculation is performed using any method known in the art, such as using a fitting method which finds a maximal difference over a single cardiac cycle, regardless of the beginning point of the maximal difference in the cardiac cycle. Alternatively, the maximum is determined as the difference between global maximum and minimum values on the graph. Further alternatively, the local minimum and maximum points on the graph are determined and the graph is divided into separate cardiac cycles. A separate difference in the cross sectional area ($\Delta A$) is determined for each cardiac cycle and a representative difference value ($\Delta A$) is optionally selected as the largest difference value. Further alternatively, the separated differences for each of the cardiac cycles are fitted to a curve yielding a maximum difference value ($\Delta A$). Further alternatively or additionally, any other suitable function of the measurements at the different applied pressures, which allows for comparison under similar conditions, is used.

Alternatively to starting with applying the pressure of the upper limit, the first measurement may be taken while applying the pressure of the lower limit, and increasing the pressure continuously up to the upper limit. In this alternative, flow restrictor 182 is optionally not included in pneumatic unit 152 (FIG. 3) and the pressure is increased gradually by restricted flow of air or any other fluid, from a pressure reservoir to cuff 124, rather than by pump 170. Further alternatively, the pressure may be applied in any other order, for example applying low pressures and high pressures intermittently.

Alternatively to applying pressure between predetermined upper and lower limits, one or more of the test rounds begin at the upper or lower limit. The applied pressure is changed continuously as described above, and the parameter is measured until the parameter value reaches a maximum and begins to decrease. At this point the test round is terminated.

In some embodiments of the invention, instead of continuously changing the pressure between the upper and lower limits while performing the measurements, a plurality of discrete pressure values are applied to the arm through measurement cuff 124 and for each applied pressure, measurements are performed over at least one cardiac cycle, in order to determine ($\Delta A$). The largest determined value of $\Delta A$ over the different pressures is used, as its applied pressure is closest to the MAP. Alternatively the differences for each pressure step are fitted to a curve yielding a maximum difference value ($\Delta A$).

The plurality of discrete pressure values may be applied in order, from lowest to highest pressure, or from highest to lowest, or may be applied not in order, with jumps between low and high pressures Applying discrete external pressure values generally achieves more accurate results than applying a continuously varying pressure, although the use of discrete external pressure values requires a longer measurement time.

In some embodiments of the invention, the parameter of the cross sectional area of the artery is an impedance measurement of a portion of the arm above the artery. Optionally, in determining the impedance, an AC current is applied between electrodes 194 and 200 (FIG. 4) and a responsive voltage is measured between electrodes 196 and 198. In some embodiments of the invention, the applied AC currents are of a frequency high enough to avoid risk to the patient but low enough so that fluids have a substantially lower impedance than muscle, flesh and skin, such that the amount of fluid (generally blood) in the arm area between electrodes 196 and 198 has a substantial affect on the measured impedance. In an exemplary embodiment of the invention, a frequency between about 30-100 kHz is used (e.g., 50 kHz).

Generally, the impedance of the arm portion between electrodes 196 and 198 can be modeled by a quasi static component $Z_0$, which does not depend on the cardiac cycle, in parallel to a time dependent component $Z(t)$, which modulates during the cardiac cycle, with the change in the amount of blood in the artery underneath the area between electrodes 196 and 198. The modulation is strongly enhanced with the application of external pressure through measurement cuff 124, such that the mean transmural pressure is about 0 and the artery moves between normal and collapsed states.

The impedance is therefore approximated by:

$$1/Z = 1/Z_0 + 1/Z(t) \tag{1}$$

The impedance of the tissue beneath sensor unit 138, except for the blood, does not change substantially with time, so that the time dependent component $Z(t)$ is mostly due to the changes in the blood content of the artery. Assuming that the time dependent component $Z(t)$ is inversely proportional to the arterial cross sectional area $A(t)$ of the artery, with a patient-specific proportionality constant K, the impedance is given by:

$$1/Z = 1/Z_0 + A(t)/K \tag{2}$$

In this embodiment, the prepared (308) graph is of values of the variations in the impedance or voltage over the cardiac cycle. The calculation of the difference between the maximal and minimal cross-sectional area is optionally performed by determining the quasi static component $Z_0$ from the graph (not shown), subtracting $Z_0$ from the graph and then determining the maximal and minimal values of the cross sectional area. The determining of the quasi static component $Z_0$ is optionally performed using a low order polynomial fit of the graph data, by smoothing the graph data in a low pass filter and/or by any other suitable averaging method. Persons experienced in the art will appreciate that various other algorithms may be used to evaluate the relative cross sectional area of the artery from the measured impedance data.

In some embodiments of the invention, the determined value of $Z(t)$ is adjusted based on the external pressure at which the maximum was found, the blood velocity of the patient, the heart rate of the patient and/or any other user attribute that affects the measured impedance.

Optionally, for simplicity, only the real part of the impedance values are considered in the above calculations, as the complex part is generally due to the cellular wall impedance which does not vary with the cardiac cycle. Alternatively, for higher accuracy, the calculations are performed using also the complex impedance and/or the absolute value of the complex impedance.

Figure 8:
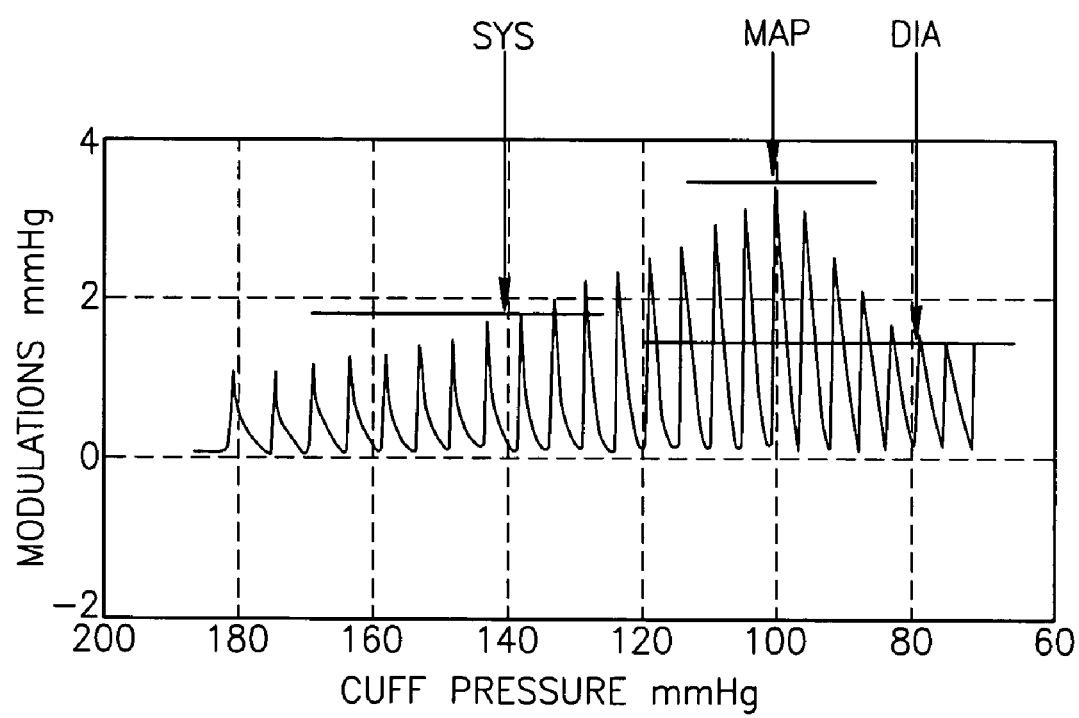
FIG. 8 is a schematic graph of pressure modulations due to changes in the amount of blood flowing through the artery, during a test in accordance with an exemplary embodiment of the present invention.

Alternatively or additionally to determining the difference in the cross-sectional area of the artery ($\Delta A$) using impedance measurements, the cross-sectional measure is determined based on pressure modulations in measurement cuff 124. As the air volume of measurement cuff 124 is large relative to the volume modulations of the artery, any changes in the volume of the arm, due to changes in the artery volume, appear as changes in the pressure of measurement cuff 124. In some embodiments of the invention, while the pressure of measurement cuff 124 is allowed to gradually decrease from the upper pressure limit to the lower pressure limit, pressure transducer 154 (FIG. 2) registers the pressure modulations in measurement cuff 124. Alternatively or additionally, a separate pressure sensor or volume sensor is mounted within measurement cuff 124, for measuring the volume modulations. Processor 150 optionally removes the quasi static air pressure in measurement cuff 124 from the registered pressure measurements. Removing the quasi static air pressure results in a graph as shown in FIG. 8 which is a schematic graph of pressure modulations due to changes in the amount of blood flowing through the artery, during a test, in accordance with an exemplary embodiment of the present invention. The extent of largest variation in pressure over a single cardiac cycle is optionally used for the difference value ($\Delta A$). The quasi static air pressure in measurement cuff 124 is optionally due to the air pressure applied by pump 170, which as described above, may vary slowly due to the air release through flow restrictor 182.

Alternatively to removing the quasi static pressure from the measured pressure in software, for example by processor 150, the quasi static pressure is removed by a hardware electronic filter, located for example at the input line or output line of A/D 158. The hardware filter may remove, for example, frequencies below about 0.5-1 Hz.

In some embodiments of the invention, in which the cross-sectional area is determined from pressure modulations in measurement cuff 124, the patient is instructed to avoid motion and remain very still, so as not to affect the measurements. Optionally, if necessary, the patient is strapped in order to avoid undesired motion.

Figure 9:
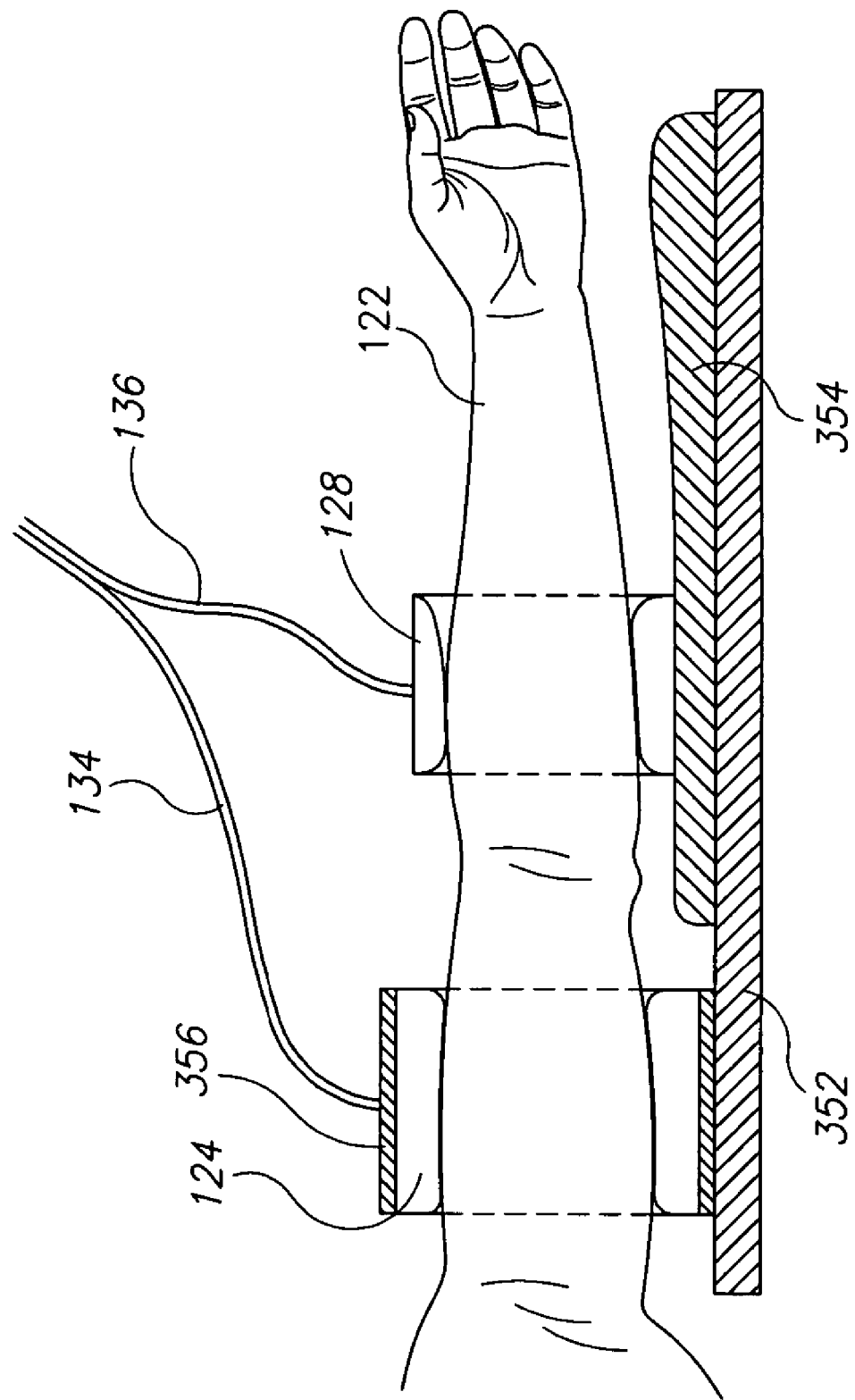
FIG. 9 is a schematic illustration of apparatus adapted to keep the patient's arm substantially still during an endothelial dysfunction test, in accordance with an exemplary embodiment of the invention.

FIG. 9 is a schematic illustration of apparatus adapted to keep the patient's arm substantially still during an endothelial dysfunction test, in accordance with an exemplary embodiment of the invention. Arm 122 optionally lies stretched out on a base plate 352. In some embodiments of the invention, a portion of base plate 352 is covered by a cushion 354, which aids in a leveled placement of arm 122 on the base plate. In an exemplary embodiment of the invention, base plate 352 is mounted at a bed side (not shown) of the patient or on a bench next to the patient. Measurement cuff 124 is optionally surrounded by a rigid cylinder 356, which supports arm 122 and prevents movement of the arm. In an exemplary embodiment of the invention, rigid cylinder 356 comprises a metal and/or a plastic frame. Occlusion cuff 128 is optionally not supported by a rigid cylinder as support is required mainly for the measurements of measurement cuff 124. Alternatively, a support cylinder is used also with occlusion cuff 128.

As mentioned above, system 50 may be used to determine the blood pressure of the patient, during endothelial dysfunction tests or separately. In some embodiments of the invention, in determining the blood pressure, measurement cuff 124 is inflated to above the systolic pressure of the patient and the air pressure of the cuff is deflated through flow restrictor 182 to below the diastolic blood pressure of the patient. During the air pressure deflation, pressure transducer 154 registers the changes in the pressure of measurement cuff 124, substantially as described above with relation to determining the difference in the cross-sectional area of the artery (ΔA) using measurement cuff 124. The resultant curve (e.g., as shown in FIG. 8) is then analyzed to find the systole (SYS), diastole (DIA) and/or MAP pressures, using any of the methods known in the art for oscillatory blood pressure measurement. For example, the MAP may be determined as the pressure of maximum modulation amplitude and the SYS and/or the DIA may be determined as the pressures at which the modulation amplitude value is an empirically predetermined fraction of the peak amplitude. Similarly, system 50 may be used to measure heart pulse rate and irregularities in pulse rate. Using system 50 generally provides blood pressure results which are less affected by patient movements, especially when the measurements are impedance measurements. This result stability is especially important in treadmill stress tests and/or in 24 hour halter blood pressure measurements.

It is noted that a poor dilatation functioning may occur due to arteriosclerosis of a specific artery. In order to prevent identification of endothelial dysfunction in patients that have local arteriosclerosis in a single artery but do not suffer from endothelial dysfunction, in some embodiments of the invention, the above method of FIG. 5, of determining the dilatation of the artery, is repeated on another artery of the patient, for example on the opposite arm. If low functioning is identified for one artery but not the other, the patient is identified as not having endothelial dysfunction and/or is sent for additional tests.

Alternatively or additionally, the method of FIG. 5 is repeated without inducing NO release, but instead inducing endothelium independent dilatation. Optionally, the repeated method includes performing a base line test, administering an endothelium independent dilatation substance, through infusion, inhalation or other means, and measuring the effect of the administered substance. If the artery dilates due to the administered endothelium independent dilatation substance but not due to occlusion or administering an endothelium stimulating substance, the patient is identified as having endothelial dysfunction. If the artery does not dilate due to the administered endothelium independent dilatation substance the test is considered invalid.

Alternatively to mounting measurement cuff 124 on the upper arm, in some embodiments of the invention, measurement cuff 124 is mounted more distally, for example on the forearm or on the wrist. It is noted, however, that in the forearm, the brachial artery branches into two arteries, namely the radial artery and the ulnar artery. The measurements are therefore based on the combined affect of the radial and ulnar arteries. If NO release by occlusion is used in these embodiments, occlusion cuff 128 is optionally placed on a more proximal portion of the arm, for example on the upper arm. Alternatively, occlusion cuff 128 is placed closer to the wrist of the patient. Further alternatively, measurement cuff 124 is used also for occlusion and system 50 does not include occlusion cuff 128. Not including occlusion cuff 124 may also be due to the use of other stimulations as described above. This alternative may be used regardless of the placement of measurement cuff 124, in order to simplify system 50. The use of an occlusion cuff separate from the measurement cuff allows the occlusion to be performed at a site not overlapping the measurement site, and hence there is less risk that the occlusion will affect the tissue on which the measurements are performed in any manner except for inducing the NO release.

Figure 10:
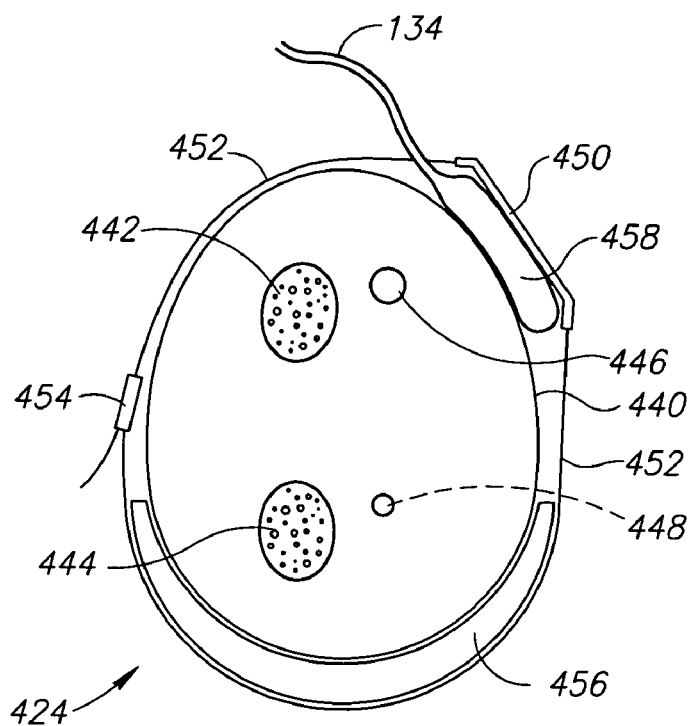
FIG. 10 is a schematic cross sectional illustration of a wrist measurement unit, in accordance with an exemplary embodiment of the invention.

FIG. 10 is a schematic cross sectional illustration of a wrist measurement unit 424 mounted on a patient wrist 440, in accordance with an exemplary embodiment of the invention. Wrist measurement unit 424 is used in these embodiments instead of measurement cuff 124 (FIG. 1), the remaining elements of system 50 optionally being substantially the same as described above with reference to FIG. 1. Occlusion cuff 128 (FIG. 1) may be placed on the forearm, the upper arm or is not used at all.

Wrist measurement unit 424 optionally includes an inflatable air cushion 458, which is connected to pneumatic unit 152 (FIG. 2) through air tube 134. Generally, wrist 440 includes a radial bone 442, an ulnar bone 444, a radial artery 446 and an ulnar artery 448. Air cushion 458 is positioned on the arm above radial artery 446 such that, when inflated, the air cushion locally presses radial artery 446 against radial bone 442 and affects the transmural pressure of the artery. Alternatively, although ulnar artery 448 has a smaller cross sectional area, air cushion 458 presses against the ulnar artery. Air cushion 458 is optionally placed on the arm close to the wrist, where radial artery 446 is relatively easily accessible. Air cushion 458 is used in accordance with any of the methods described above for using measurement cuff 124, for measurement and/or occlusion.

In some embodiments of the invention, a plate 450 attached to the wrist of the patient by a strap 452 and a fastener 454 hold air cushion 458 in place above the radial artery. Optionally, a cushion 456 protects the patient's arm opposite air cushion 458 from strap 452. In some embodiments of the invention, in which wrist measurement unit 424 is used with bio-impedance measurements, a bio-impedance sensor unit, similar to sensor unit 138, is mounted on air cushion 458 and/or on strap 452 along side or beneath the air cushion.

The use of wrist measurement unit 424 mounted over the radial artery, unlike measurement cuff 124, allows performing endothelial dysfunction measurements, which affect the blood flow in radial artery 446, substantially without affecting the blood flow through ulnar artery 448 and the veins.

Thus, in some embodiments of the invention, continuous lengthy measurements, for a duration of several minutes or even more, may be performed before and/or after the occlusion with only minimal interruption of the blood flow to the hand. As the pressure only blocks the artery for part of the cardiac cycle, blood is allowed to flow to the hand. Having the veins open for return blood flow, allows flow of blood to and from the hand. Performing the measurements over a relatively long duration of several minutes provides more accurate results, especially for determining the volution of the dilatation with time.

In some embodiments of the invention, the continuous measurements include repeated tests performed one after the other, substantially without a recess between tests, each test including measurements taken between the upper and lower pressure levels. Alternatively, a single scanning between the upper and lower pressure levels is performed to determine the MAP pressure, and thereafter measurements of the parameter related to the artery cross-section area are continuously taken while applying a fixed pressure at the determined MAP. In some embodiments of the invention, a short pressure scanning around the applied pressure (e.g., +5 mmHG in each direction) is performed periodically to find the new MAP in case the MAP of the patient drifted.

Figure 11:
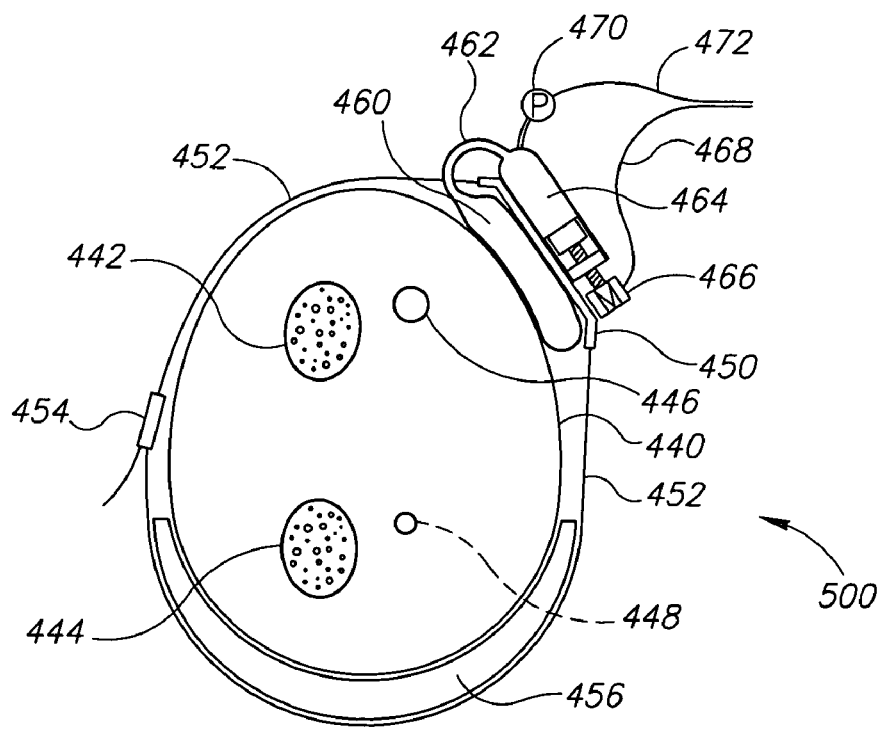
FIG. 11 is a schematic cross sectional illustration of a wrist measurement unit, in accordance with another exemplary embodiment of the invention.

FIG. 11 is a schematic cross sectional illustration of a wrist measurement unit 500, in accordance with another exemplary embodiment of the invention. Wrist measurement unit 500 differs from wrist measurement unit 424 (FIG. 10) in that hydraulic pressure is used instead of pneumatic pressure. Wrist measurement unit 500 includes an hydraulic liquid cushion 460, which is connected through a tube 462 to a piston 464. The pressure in liquid cushion 460 is optionally increased or decreased by operation of a motor 466 which in turn is controlled by microprocessor 150 via a cable 468. The pressure in liquid cushion 460 is optionally measured by a transducer 470 which is connected to A/D 158 (FIG. 2) through a cable 472.

Wrist measurement unit 500 is used according to any of the procedures described above. It is noted, however, that some of the procedures are more fit for hydraulic pressure control, for example procedures in which the applied pressure moves up from the low pressure limit to the upper pressure limit and/or procedures including applying fixed discrete pressure levels.

Alternatively to using pneumatic or hydraulic force to apply pressure to the artery, any other method may be used to apply the pressure, such as using an electronic or other motor rotating a screw and/or a screw system that fastens a strap which presses on the artery. In some embodiments of the invention, a combination of different methods may be used in applying the force. For example, one method (e.g., pneumatic) may be used to apply a base pressure at the lower limit and a second method (e.g., hydraulic) may be used for fine tuning up to the upper limit.

As described above, the cross-sectional area difference (ΔA) is determined at the MAP pressure where the maximal cross-sectional difference is reached. Thus, the comparison of the dilated difference and the base-line difference is based on equal conditions, i.e., in each phase the artery is allowed to reach its maximum. Alternatively, the measurements are performed at a different point which allows comparison of the dilated and baseline values. In an exemplary embodiment of the invention, the parameter value is measured at a central point between systole and diastole. The diastole and systole points are optionally repeatedly determined, at least once for each measurement round, so that the parameter values are determined as close as possible to the measurement pressure.

In some embodiments of the invention, different methods of selecting the pressure at which the test is performed are used before and after inducing the NO release. Optionally, before NO release, pressures between the upper and lower limits are scanned in search for a pressure at which a highest cross-sectional area difference (ΔA) is achieved. After NO release, a single pressure level, equal to the pressure found to achieve a highest cross-sectional area difference (ΔA) before the NO release, is used. Alternatively, after NO release, the scanning is performed over a shorter range around the MAP determined before inducing the NO release. These embodiments may be used, for example for patients having a relatively regular heart cycle.

Further alternatively or additionally, one or more of the measurement rounds is performed at a fixed pressure different from the MAP but within the limits between systole and diastole. In an exemplary embodiment of the invention, some or all of the measurements are performed at an anchor pressure, different from the MAP, which allows comparison of measurements performed at different times, even if the blood pressure of the patient changes.

In some embodiments of the invention, microprocessor 150 is programmed to carry out a complete test session automatically without requiring instructions from a human operator. Optionally, control unit 132 checks that the conditions are proper and stops the test session if a problem is detected, for example when no sensible maximum was found (maybe due to drastic changes in the blood pressure of the patient during the test). Alternatively, the operation sequence of a test session may be partially or entirely human operated. For example, each measurement phase may be controlled automatically by microprocessor 150, while the initiation of each phase is controlled by a human operator. Optionally, an operator may program operation sequences through computer 146. Alternatively or additionally, required operation sequences are preprogrammed into microprocessor 150 at the time of manufacture.

Alternatively or additionally to comparing the difference cross-sectional area before the stimulus is applied and after the stimulus is applied, measurements for the base line value (at which the stimulus does not affect the measurements) are performed a settling time after the stimulus is applied, when the stimulus does not affect the artery cross-sectional area. Although this alternative requires a longer test, it is more accurate, as the occlusion (which could change the patient's condition) does not separate between the measurements. Further alternatively or additionally, base line measurements are performed both before and after the dilated measurements are performed and the value used is taken as a function of both the measurements.

It will be appreciated that the above described methods and apparatus may be varied in many ways, including, changing the order of acts of the methods, and the exact implementation used for the apparatus. It should also be appreciated that the above described methods and apparatus are to be interpreted as including apparatus for carrying out the methods and methods of using the apparatus.

The present invention has been described using non-limiting detailed descriptions of embodiments thereof that are provided by way of example and are not intended to limit the scope of the invention. For example, rather than performing the endothelial dysfunction test on the arm, the method may be performed on a patient's leg. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe a particular mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

The invention claimed is:

1. Apparatus for assessment of relative changes in the cross sectional area of a limb artery, comprising:
  a measurement cuff adapted to apply a pressure to an artery;
  a measurement unit adapted to determine, over one or more cardiac cycles, a value for a parameter related to the cross-sectional area of the artery, while the pressure is applied;
  a controller adapted to apply to the cuff a pressure that causes the cross-sectional area of the artery to change between systole and diastole much more than if the pressure is not applied, and to induce at least two measurement rounds of the parameter by the measurement unit while the pressure is applied;
  wherein the controller is adapted to induce at least one of the measurement rounds responsive to an indication that a stimulus was administered to the artery and at least one of the measurement rounds before the indication that the stimulus was administered to the artery is received; and
  a processor adapted to compare the values determined by the measurement unit in the at least two measurement rounds; wherein
  the controller is adapted to apply a pressure between the diastole and systole pressure levels of the artery such that the artery collapses in diastole and recuperates in systole.

2. Apparatus according to claim 1, wherein the measurement cuff includes a hydraulic or pneumatic pump adapted to apply the pressure.

3. Apparatus according to claim 1, wherein the measurement cuff includes a motor adapted to pull a strap that applies the pressure.

4. Apparatus according to claim 1, wherein the cuff is adapted to apply the pressure substantially around an entire circumference of a limb including the artery.

5. Apparatus according to claim 1, wherein the measurement cuff is adapted to apply a local pressure which does not substantially affect other blood vessels in a same limb as the artery.

6. Apparatus according to claim 1, wherein the measurement unit is adapted to measure a bio-impedance.

7. Apparatus according to claim 6, wherein the measurement unit includes disposable electrodes.

8. An apparatus according to claim 6, wherein the controller is adapted to apply pressure to the cuff and to measure an impedance through the measurement unit, substantially concurrently.

9. An apparatus according to claim 8, wherein the measurement unit is comprised of at least four electrodes when sensing bio-impedance.

10. An apparatus according to claim 6, wherein the measurement unit comprises an alternating current source and an alternating voltage measurement unit.

11. Apparatus according to claim 1, wherein the controller is adapted to apply the pressure continuously over at least five cardiac cycles of the patient.

12. Apparatus according to claim 1, wherein the controller is adapted to apply a pressure substantially equal to the mean artery pressure of the artery.

13. Apparatus according to claim 1, wherein the controller is adapted to apply a plurality of different pressure levels during a single measurement round.

14. Apparatus according to claim 13, wherein the controller is adapted to apply a continuously changing pressure.

15. Apparatus according to claim 1, wherein the processor is adapted to calculate a change in the cross-sectional area of the artery over a single cardiac cycle of each of the measurement rounds and to compare the calculated changes of the measurement rounds.

16. Apparatus according to claim 15, wherein the processor is adapted to select, for each measurement round, a single cardiac cycle from the one or more cardiac cycles for which the parameter value was determined and to calculate the change for the selected cardiac cycle.

17. Apparatus according to claim 1, wherein the processor is adapted to estimate an envelope of the measured parameter values and find a maximal parameter value difference from the envelope.

18. Apparatus according to claim 1, wherein the measurement cuff or parts thereof are disposable.

19. An apparatus according to claim 1, wherein the measurement cuff is further adapted to apply a stimulus to the artery.

20. An apparatus according to claim 19, wherein the measurement cuff is adapted to apply the stimulus by occlusion of a blood vessel.

21. An apparatus according to claim 1, wherein the controller is adapted to administer at least one drug to a patient as a stimulus.

22. An apparatus according to claim 1, wherein the controller is adapted to calculate an endothelial functioning score, responsive to the impedance measurements.

23. An apparatus according to claim 1, wherein the processor is adapted to provide a score indicative of the endothelial function of the artery based on the values determined by the measurement unit in the at least two measurement rounds.

24. Apparatus for assessment of relative changes in the cross sectional area of a limb artery, comprising:
  a measurement cuff adapted to apply a pressure to an artery;
  a measurement unit adapted to determine, over one or more cardiac cycles, a value for a parameter related to the cross-sectional area of the artery, while the pressure is applied;
  a controller adapted to apply to the cuff a pressure that causes the cross-sectional area of the artery to change between systole and diastole much more than if the pressure is not applied, and to induce at least two measurement rounds of the parameter by the measurement unit while the pressure is applied; and a processor adapted to compare the values determined by the measurement unit in the at least two measurement rounds;
  further comprising a second measurement cuff wherein the measurement cuff and the second measurement cuff are adapted to restrict the flow of blood and apply the pressure on the artery, respectively;

wherein the measurement cuff is further adapted to apply a stimulus to the artery by occlusion of a blood vessel.

25. An apparatus according to claim 24, wherein the controller is adapted to restrict the flow of blood through the artery for at least 3 minutes using the measurement cuff.

26. An apparatus according to claim 24, wherein the processor is adapted to provide a score indicative of the endothelial function of the artery based on the values determined by the measurement unit in the at least two measurement rounds.

27. An apparatus according to claim 26, wherein the score is additionally a function of at least one patient attribute.

28. Apparatus for assessment of relative changes in the cross sectional area of a limb artery, comprising:
- a measurement cuff adapted to apply a pressure to an artery;
- a measurement unit adapted to determine, over one or more cardiac cycles, a value for a parameter related to the cross-sectional area of the artery, while the pressure is applied;
- a controller adapted to apply to the cuff a pressure that causes the cross-sectional area of the artery to change between systole and diastole much more than if the pressure is not applied, and to induce at least two measurement rounds of the parameter by the measurement unit while the pressure is applied; and
- a processor adapted to compare the values determined by the measurement unit in the at least two measurement rounds;
- wherein the measurement unit is adapted to measure a bio-impedance; and
- wherein the controller is adapted to apply pressure to the cuff and to measure an impedance through the measurement unit, substantially concurrently; and
- wherein the controller is adapted to calculate an endothelial functioning score, responsive to the impedance measurements.

29. Apparatus according to claim 28, wherein the measurement cuff includes a hydraulic or pneumatic pump adapted to apply the pressure.

30. Apparatus according to claim 28, wherein the measurement cuff includes a motor adapted to pull a strap that applies the pressure.

31. Apparatus according to claim 28, wherein the cuff is adapted to apply the pressure substantially around an entire circumference of a limb including the artery.

32. Apparatus according to claim 28, wherein the measurement cuff is adapted to apply a local pressure which does not substantially affect other blood vessels in a same limb as the artery.

33. Apparatus according to claim 28, wherein the measurement unit includes disposable electrodes.

34. Apparatus according to claim 28, wherein the controller is adapted to induce at least one of the measurement rounds responsive to an indication that a stimulus was administered to the artery and at least one of the measurement rounds before the indication that the stimulus was administered to the artery is received.

35. Apparatus according to claim 28, wherein the controller is adapted to apply the pressure continuously over at least five cardiac cycles of the patient.

36. Apparatus according to claim 28, wherein the controller is adapted to apply a pressure between the diastole and systole pressure levels of the artery such that the artery collapses in diastole and recuperates in systole.

37. Apparatus according to claim 28, wherein the controller is adapted to apply a pressure substantially equal to the mean artery pressure of the artery.

38. Apparatus according to claim 28, wherein the controller is adapted to apply a plurality of different pressure levels during a single measurement round.

39. Apparatus according to claim 38, wherein the controller is adapted to apply a continuously changing pressure.

40. Apparatus according to claim 28, wherein the processor is adapted to calculate a change in the cross-sectional area of the artery over a single cardiac cycle of each of the measurement rounds and to compare the calculated changes of the measurement rounds.

41. Apparatus according to claim 40, wherein the processor is adapted to select, for each measurement round, a single cardiac cycle from the one or more cardiac cycles for which the parameter value was determined and to calculate the change for the selected cardiac cycle.

42. Apparatus according to claim 28, wherein the processor is adapted to estimate an envelope of the measured parameter values and find a maximal parameter value difference from the envelope.

43. Apparatus according to claim 28, wherein the measurement cuff or parts thereof are disposable.

44. An apparatus according to claim 28, wherein the measurement cuff is further adapted to apply a stimulus to the artery.

45. An apparatus according to claim 44, wherein the measurement cuff is adapted to apply the stimulus by occlusion of a blood vessel.

46. An apparatus according to claim 45, further comprising a second measurement cuff wherein the measurement cuff and the second measurement cuff are adapted to restrict the flow of blood and apply the pressure on the artery, respectively.

47. An apparatus according to claim 46, wherein the controller is adapted to restrict the flow of blood through the artery for at least 3 minutes using the measurement cuff.

48. An apparatus according to claim 28, wherein the processor is adapted to provide a score indicative of the endothelial function of the artery based on the values determined by the measurement unit in the at least two measurement rounds.

49. An apparatus according to claim 48, wherein the score is additionally a function of at least one patient attribute.

50. An apparatus according to claim 28, wherein the measurement unit is comprised of at least four electrodes when sensing bio-impedance.

51. An apparatus according to claim 50, wherein the measurement unit comprises an alternating current source and an alternating voltage measurement unit.

52. An apparatus according to claim 28, wherein the controller is adapted to administer at least one drug to a patient as a stimulus.

* * * * *